United States Patent
Sell et al.

(10) Patent No.: US 6,926,729 B1
(45) Date of Patent: Aug. 9, 2005

(54) LOW PROFILE VALVE AND METHOD OF MAKING

(75) Inventors: Jonathan C. Sell, West St. Paul, MN (US); Hans G. Mische, St. Cloud, MN (US); Jon D. Gamble, Minneapolis, MN (US); Scott A. Hoium, Coon Rapids, MN (US); Charles R. Lucht, Minneapolis, MN (US); Thomas J. Wilke, Alex., MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/547,779

(22) Filed: Apr. 12, 2000

Related U.S. Application Data

(63) Continuation of application No. 08/697,523, filed on Aug. 26, 1996, now Pat. No. 6,090,083, which is a continuation-in-part of application No. 08/594,714, filed on Jan. 31, 1996, now abandoned.

(51) Int. Cl.$^7$ ............................................. A61M 29/00
(52) U.S. Cl. ..................... 606/192; 606/194; 604/249; 604/99.02; 604/920
(58) Field of Search ................................ 604/249, 240, 604/96.01, 920, 30, 33, 97.01, 99.04, 99.01, 604/99.02, 99.03, 102.01, 102.02, 97.02; 606/191–194

(56) References Cited

U.S. PATENT DOCUMENTS

| | | |
|---|---|---|
| 3,044,468 A | 7/1962 | Birtwell |
| 3,087,492 A | 4/1963 | Garth ........................... 128/350 |
| 3,192,949 A | 7/1965 | De See |
| 3,211,150 A | 10/1965 | Foderick ...................... 128/349 |
| 3,726,282 A | 4/1973 | Patel |
| 3,799,171 A | 3/1974 | Patel |
| 3,908,267 A | 9/1975 | Loyd et al. .................... 29/631 |
| 3,982,544 A * | 9/1976 | Dyck ........................... 604/159 |
| 4,026,298 A * | 5/1977 | Grausz ................. 128/DIG. 25 |
| 4,028,037 A | 6/1977 | Dawson ...................... 425/392 |

(Continued)

FOREIGN PATENT DOCUMENTS

EP    0 272 112 A2    6/1988

(Continued)

*Primary Examiner*—Cris L. Rodriguez
(74) *Attorney, Agent, or Firm*—Crompton, Seager & Tufte, LLC

(57) ABSTRACT

A low profile inflation valve located inside a balloon catheter that enables a user to inflate the balloon and exchange other medical apparatus over the catheter while the balloon remains inflated.

The low profile inflation valve of the present invention includes a first tube having a lumen and at least one region of decreased inner diameter, and a structure movably located inside the lumen of said first tube, wherein said region of decreased inner diameter of said first tube forms a seal with a portion of said structure. The present invention further includes a method of making a low profile inflation valve using a first and second tube comprising the steps of creating an aperture in at least one side of a second tube, placing the second tube inside a first tube, the first tube being made of thermoplastic material, applying heat to a localized area of the first tube, and compressing the first tube to form a region of reduced internal diameter, the reduced diameter forming a seal with the outside diameter of the second tube.

17 Claims, 3 Drawing Sheets

U.S. PATENT DOCUMENTS

| | | | |
|---|---|---|---|
| 4,088,135 A | | 5/1978 | O'Neill |
| 4,205,683 A | * | 6/1980 | O'Neill .................... 604/920 |
| 4,205,691 A | | 6/1980 | Patel ......................... 128/774 |
| 4,318,410 A | * | 3/1982 | Chin .......................... 604/271 |
| 4,333,452 A | | 6/1982 | Au ....................... 128/205.24 |
| 4,506,691 A | | 3/1985 | Tseo ............................. 137/1 |
| 4,517,979 A | | 5/1985 | Pecenka .................... 128/325 |
| 4,614,188 A | * | 9/1986 | Bazell et al. .......... 604/101.05 |
| 4,646,742 A | | 3/1987 | Packard et al. |
| 4,710,168 A | | 12/1987 | Schwab et al. |
| 4,723,547 A | * | 2/1988 | Kullas et al. ............... 604/909 |
| 4,800,109 A | | 1/1989 | Washizu .................... 428/34.9 |
| 4,856,510 A | * | 8/1989 | Kowalewski .......... 128/207.14 |
| 4,902,095 A | | 2/1990 | Baker et al. ............. 350/96.21 |
| 4,921,483 A | | 5/1990 | Wijay et al. |
| 4,923,498 A | | 5/1990 | Gregory ...................... 65/109 |
| 4,968,306 A | | 11/1990 | Huss et al. ................. 604/264 |
| 5,015,233 A | | 5/1991 | McGough et al. |
| 5,022,422 A | | 6/1991 | di Palma |
| 5,059,176 A | | 10/1991 | Winters ....................... 604/96 |
| 5,061,240 A | | 10/1991 | Cherian |
| 5,085,636 A | | 2/1992 | Burns |
| 5,167,239 A | | 12/1992 | Cohen et al. ............... 128/772 |
| 5,171,221 A | | 12/1992 | Samson ....................... 604/96 |
| 5,259,839 A | | 11/1993 | Burns |
| 5,297,546 A | | 3/1994 | Spofford et al. |
| 5,304,198 A | | 4/1994 | Samson |
| 5,306,246 A | | 4/1994 | Sahatjian et al. |
| 5,320,604 A | * | 6/1994 | Walker et al. ......... 604/101.03 |
| 5,336,174 A | | 8/1994 | Daoud et al. ................. 604/30 |
| 5,378,238 A | | 1/1995 | Peters et al. |
| 5,423,742 A | | 6/1995 | Theron ......................... 604/28 |
| 5,449,343 A | | 9/1995 | Samson et al. ............... 604/96 |
| 5,496,310 A | | 3/1996 | Exconde et al. |
| 5,536,252 A | | 7/1996 | Imran et al. ................. 604/101 |
| 5,545,133 A | | 8/1996 | Burns et al. .................. 604/96 |
| 5,695,468 A | | 12/1997 | Lafontaine et al. ........... 604/96 |
| 5,709,653 A | | 1/1998 | Leone |
| 5,785,685 A | | 7/1998 | Kugler et al. ................. 604/96 |
| 5,807,330 A | | 9/1998 | Teitelbaum .................. 604/96 |
| 5,833,644 A | | 11/1998 | Zadno-Azizi et al. ......... 604/52 |
| 5,833,650 A | | 11/1998 | Imran ........................... 604/53 |
| 5,944,716 A | | 8/1999 | Hektner |
| 6,090,083 A | | 7/2000 | Sell et al. |
| 6,102,891 A | * | 8/2000 | Maria van Erp ............ 604/920 |
| 6,260,552 B1 | | 7/2001 | Mortier et al. |
| 6,355,014 B1 | * | 3/2002 | Zadno-Azizi et al. .. 604/167.03 |

FOREIGN PATENT DOCUMENTS

| | | |
|---|---|---|
| EP | 0 547 358 A2 | 6/1993 |
| EP | 0 547 358 A3 | 10/1993 |
| EP | 0 569 030 A1 | 11/1993 |
| EP | 0 710 490 A2 | 5/1996 |
| EP | 0 710 490 A3 | 12/1996 |
| EP | 0 769 307 A2 | 1/1998 |
| GB | 2 139 725 A | 11/1984 |
| GB | 2277875 A | 11/1994 |
| JP | 56-152655 A | 11/1981 |
| JP | 1-232927 A | 9/1989 |
| WO | WO 92/13589 A1 | 8/1992 |
| WO | WO 97/44082 A2 | 11/1997 |
| WO | WO 97/44085 A2 | 11/1997 |
| WO | WO 98/38930 A1 | 9/1998 |
| WO | WO 99/26692 A1 | 6/1999 |
| WO | WO 99/42161 A2 | 8/1999 |
| WO | WO 99/45835 A2 | 9/1999 |

* cited by examiner

LOW PROFILE VALVE AND METHOD OF MAKING

CROSS REFERENCE TO RELATED APPLICATION

This application is continuation of Ser. No. 08/697,523 filed on Aug. 26, 1996, now U.S. Pat. No. 6,090,083, which is a continuation in part of application Ser. No. 08/594,714 filed Jan. 31, 1996 now abandoned.

BACKGROUND OF THE INVENTION

This invention relates to the field of medical apparatus. More specifically, this invention pertains to a low profile valve for use with medical catheters.

Catheters are commonly used for a multitude medical procedures. Many prior art intravascular medical assemblies which incorporate catheters lack simple, effective means for regulating the pressure in the catheter or maintaining a pressure difference between the elements of the system. In addition, it is often difficult to control the flow of a fluid traveling in the catheter.

Valves are commonly used in an attempt to address these problems. However, many prior art valves increase the profile of existing intravascular medical assemblies. This makes exchange of various intravascular apparatus, such as sheaths, balloons and guides, over the valve either difficult or impossible. A device that is small enough to be used intravascularly and effectively controls the pressure inside the catheter would be a great improvement in the art.

SUMMARY OF THE INVENTION

In one aspect, the low profile inflation valve of the present invention comprises a first tube having a lumen and at least one region of a first length with decreased inner diameter, a second tube slidably engaged with the lumen of the first tube, the second tube having a lumen and a closed distal end extending distally past said region of decreased inner diameter of the first tube, the second tube also having at least one aperture allowing passage of fluid from the lumen of the second tube to the lumen of the first tube and a stop attached to the second tube distally of the aperture, the stop having a transverse dimension greater than the decreased inner diameter of the first tube.

In the second aspect, the low profile inflation valve of the present invention comprises a first tube having a lumen that is closed at its distal end, the first tube also comprises at least one region with a decreased inner diameter and a second tube located inside the first tube, the second tube having a lumen and a closed distal end, the second tube also having at least one aperture located near its distal end, at least a portion of the second tube extending past the region of decreased inner diameter of the first tube when the valve is in an open position, wherein the region of decreased inner diameter of the first tube forms a seal with the outer diameter of the second tube and blocks the aperture when the valve is in a closed position.

In the third aspect, the present invention comprises a balloon catheter assembly comprising a low profile inflation valve comprising a first tube having a lumen with a closed distal end, the first tube also having one region with a decreased inner diameter, a second tube located inside the first tube, the second tube having a lumen and a closed distal end extending distally past said region of decreased inner diameter of said first tube, the second tube also having at least one aperture allowing passage of fluid from the lumen of the second tube to the lumen of the first tube when the valve is in an open position, a stop attached to the second tube distally of the aperture, the stop having a transverse dimension greater than the decreased inner diameter of the first tube, and an elastomeric balloon in fluid communication with the lumen of said first tube distally of the region of decreased inner diameter.

In the fourth aspect, the present invention comprises a method of making a low profile inflation valve using a first and second tube comprising the steps of creating an aperture in at least one side of a second tube, placing the second tube inside a first tube, the first tube being made of thermoplastic material, applying heat to a localized area of the first tube, and compressing the first tube to form a region of reduced internal diameter, the reduced diameter forming a seal with the outside diameter of the second tube.

In the fifth aspect, the present invention comprises a method of making a balloon catheter and valve assembly comprising the steps of supplying a balloon catheter having a balloon and an inflation lumen, providing a hypotube having at least one aperture located near its distal end, the hypotube also having a stop attached to its distal end, inserting the hypotube into the inflation lumen of the balloon catheter, loading a teflon sleeve onto the outer diameter of the catheter, the sleeve having an inner diameter that is larger than the outer diameter of the catheter, loading the catheter-hypotube-sleeve assembly into a resistively heated die, heating the assembly to just above the softening point of the catheter until the catheter wall in the region of the sleeve is softened, compressing the assembly in the region of the sleeve to form a region of reduced internal diameter and cooling the assembly.

In the sixth aspect, the present invention comprises a method of making a tube with a region of decreased internal diameter comprising the steps of applying heat to a localized area of a tube sufficient to soften the tube wall material in that region and compressing the tube, thereby causing the tube wall in the heated region to form said region of decreased internal diameter.

In the seventh aspect, the present invention comprises a low profile inflation valve comprising a first tube having a lumen and at least one region with a decreased inner diameter, and a structure movably located inside the first tube, wherein the region of decreased inner diameter of the first tube forms a seal with a portion of the structure.

In the eighth aspect, the present invention comprises a low profile inflation valve located inside a balloon catheter that enables a user to maintain the balloon in an inflated state and exchange other medical apparatus over the catheter.

In the ninth aspect, the invention comprises a valve having a maximum outer profile of about 0.3 cm.

One of the many advantages of the low profile valves of the present invention is that they provide a simple, effective means for regulating the pressure in a catheter or maintaining a pressure difference between the elements of a system. A second advantage is that these valves enable a user to control the flow of fluid in the catheter. In addition, these valves are small enough to be used intravascularly. Furthermore, when used in a balloon catheter, they enable a user to maintain the balloon in an inflated state while exchanging other medical apparatus over the catheter.

DETAILED DESCRIPTION OF THE DRAWINGS AND PREFERRED EMBODIMENTS OF THE INVENTION

Figure 1:
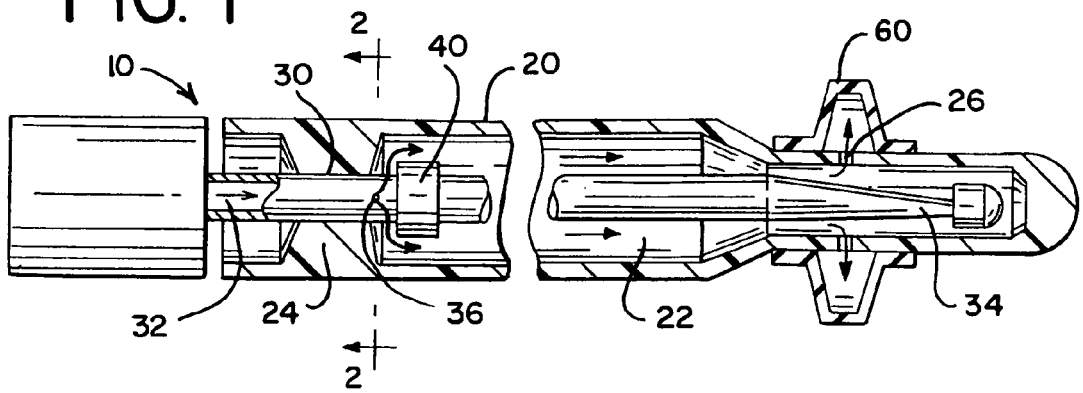
FIG. 1 is a cross-sectional side view of the first preferred embodiment of the low profile inflation valve of the present invention in the inflation position.

Referring initially to FIG. 1, a preferred embodiment of the low profile inflation valve 10 of the present invention is disclosed. As illustrated, the valve 10 includes a first tube 20. In the preferred embodiment, the first tube 20 is part of a catheter. The first tube 20 has a central lumen 22 and a region of a first length of decreased inner diameter 24. The lumen need not have a circular cross-section. As used herein, the term "decreased inner diameter" includes a decreased cross-sectional area where the lumen is not round. The length of the region 24 may vary considerably. Preferably, the region of decreased inner diameter 24 is between about 0.1 and about 2.0 cm long. In the preferred embodiment, the first tube 20 has an outer diameter that is uniform over its length.

The valve 10 also includes a second tube 30 slidably engaged within the lumen 22 of the first tube 20. The second tube 30 also has a lumen 32 and a closed distal end 34. The second tube 30 also has at least one aperture 36 located near its distal end 34. When the valve 10 is fully assembled, the aperture 36 allows passage of fluid from the lumen 32 of the second tube 30 to the lumen 22 of the first tube 20. The second tube 30 is precisely situated inside the first tube 20 so that at least a portion of the second tube 30 extends distally past the region of decreased inner diameter 24 of the first tube 20. The region of decreased inner diameter 24 of the first tube 20 and the outer diameter of the second tube 30 form a seal. Because the second tube 30 is slidably engaged in the first tube 20, in the preferred embodiment, the valve 10 also has a stop 40 attached to the second tube 30 distally of aperture 36. In the preferred embodiment, the outside diameter of the first tube 20 is between about 0.03 and about 1.0 cm, preferably between about 0.07 and about 0.2 cm, the inside diameter of the tube 20 is between about 0.03 and about 1.0 cm, preferably about 0.03 and about 0.2 cm, except in its region of reduced diameter, where the inside diameter is between about 0.03 and about 1.0 cm, preferably about 0.03 and about 0.2 cm. In the preferred embodiment, the second tube 30 has an outside diameter the same as the inside diameter of the region of decreased inner diameter of the first tube 20 and an inside diameter of between about 0.03 and about 1.0 cm, preferably between about 0.03 and about 0.2 cm. In the preferred embodiment, the stop 40 is located approximately 0.1–4.0 cm from the aperture 36 in the second tube 30, more preferably about 1.3 cm and most preferably about 0.64 cm. The stop 40 has a transverse dimension greater than the decreased inner diameter of the first tube 20 and thus limits the distance of proximal travel of the second tube 30. The catheter preferably also includes a polymeric balloon 60. The balloon 60 may be a separate component attached to the first tube 20, or it may be blown out of the first tube 20. If the balloon 60 is a separate component, the first tube 20 contains a balloon inflation aperture 26 which permits fluid to travel into the balloon 60 from the catheter lumen 22, and vice versa.

Figure 2:
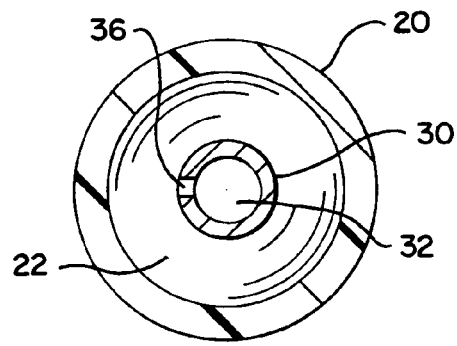
FIG. 2 is a cross-sectional front view of the valve of FIG. 1 taken along the line 2—2 of FIG. 1.

The low profile inflation valve 10 of the present invention may accomplish various functions depending on the position of aperture 36. Thus, the valve 10 may be used to inflate a balloon 60, to retain the pressure inside the balloon 60 or to deflate the balloon 60. For example, in FIGS. 1 and 2, the second tube 30 is pushed forward by the operator so that aperture 36 is positioned distally of the region of reduced inner diameter 24 of the first tube 20. In this position, fluid that is pumped into the lumen 32 of the second tube 30 exits the second tube 30 through aperture 36 and enters the catheter lumen 22. The fluid travels through the catheter lumen 22 until it reaches a balloon inflation aperture 26. The inflation fluid exits the catheter lumen 22 through the balloon inflation aperture 26 and thus inflates the balloon 60. Note that the valve could also be designed so that the second tube 30 is pulled backward by the operator when inflating or deflating the balloon. Again, the aperture 36 resides within a region of reduced inner diameter 24 until inflation or deflation is necessary. Such a design may incorporate two or more areas of reduced internal diameter.

Figure 3:
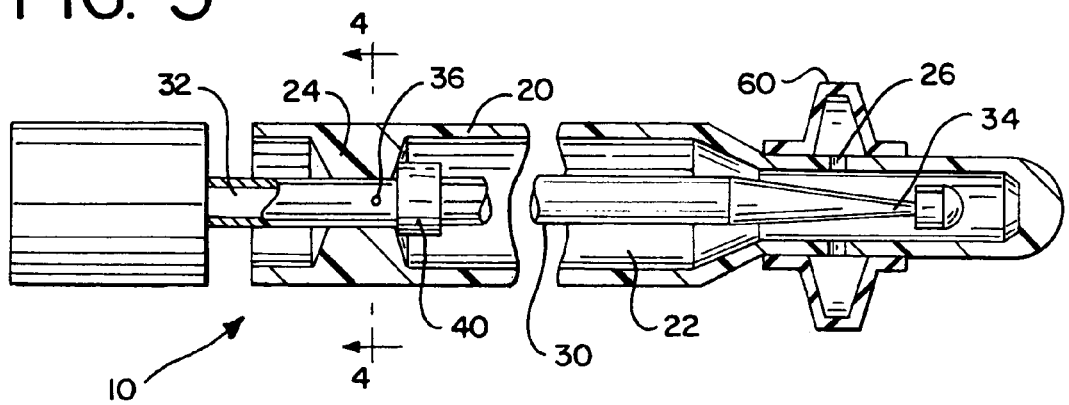
FIG. 3 is a cross-sectional side view of the valve of FIG. 1 in the closed position.
Figure 4:
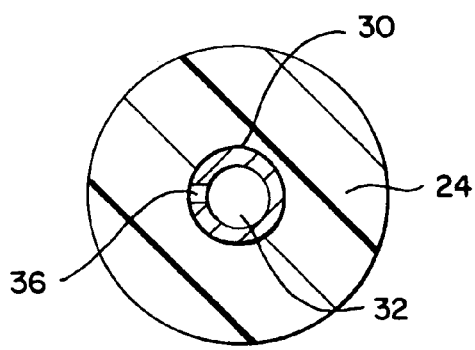
FIG. 4 is a cross-sectional front view of the valve of FIG. 3 taken along the line of 4—4 of FIG. 3.

When the pressure inside the balloon 60 reaches the desired level, the operator moves the second tube 30 in the proximal direction such that aperture 36 is positioned within the region of reduced inner diameter 24 of the first tube 20 or proximal to the region of reduced inner diameter 24 of the first tube. As most clearly depicted in FIG. 3, the stop 40 attached to the second tube 30 limits the distance of proximal travel of the second tube 30. FIG. 4 illustrates the position of the aperture 36 against the wall of the first tube 20. Because a low pressure seal is formed between the outer diameter of the second tube 30 and the region of reduced diameter 24 of the first tube 20, the fluid is prevented from exiting the catheter lumen through aperture 36.

In the event that it is no longer necessary to maintain the balloon 60 in an inflated state, the user returns the valve 10 to the position depicted in FIG. 1. Thus, the second tube 30 is moved in the proximal direction so that aperture 36 is located distally of the region of reduced inner diameter 24 of the first tube 20. When pressure is released from the lumen of the second tube 30, the inflation fluid will exit the balloon 60 and enter the catheter lumen 22 through the balloon inflation aperture 26. The inflation fluid travels proximally and enters the lumen 32 of the second tube 30 through aperture 36. Thus, the balloon 60 is deflated.

The first tube 20 is preferably made of thermoplastic material. More preferably, the first tube 20 is Pebax, manufactured by Atochem.

The second tube may be made of any biocompatible metal or biocompatible polymer. The second tube 30 is preferably made of a rigid polymer or metal, more preferably a high temperature polymer, and most preferably stainless steel or Nitinol. Examples of high temperature polymers include, but are not limited to, PEEK, polyamide, and Teflon. When the valve is made by the preferred method described below, the second tube 30 must have a higher melting point than the first tube 20.

The stop 40 may be formed by any material and any method that gives a portion of the second tube an outer diameter greater than the reduced inner diameter of the first tube. Examples of such materials include but are not limited to metals and various polymers. For example, the stop may be a piece of coil or short section of tube glued or soldered onto the second tube.

The invention also includes the method of making the above described low profile inflation valve 10 using a first 20 and second tube 30. Initially, the distal end of the second tube 30 is sealed. Sealing may be accomplished by any method currently known in the art. Preferably, either before or after the end 34 is sealed, an aperture 36 is created in at least one side of the second tube 30. The aperture 36 should preferably be located between about 0.1 and about 2.0 cm from the distal end of the second tube 30, more preferably about 0.3 to about 1.7 cm from the distal end of the second tube 30 and most preferably about 0.5 cm from the distal end of the second tube 30. Then the second tube 30 is placed inside the first tube 20. In the preferred embodiment, the first tube 20 is a balloon catheter. If the compositions of the first 20 and second 30 tubes create the potential for the tubes to stick together, the second tube 30 may be covered with a lubricous sleeve or coating before it is placed in the first tube 20. Preferably, the lubricous coating is permanently sprayed on the tube. Examples of suitable coatings include, but are not limited to, Teflon, silicone and HPC (hydrophilic coating). Alternately, a sleeve made of similar material, such as Teflon, could be placed onto the outer diameter of the second tube. The sleeve must have an inner diameter that is larger than the outer diameter of the second tube. If the first tube is a balloon catheter, it is preferred that the distal end of the sleeve is approximately 0.25 in. from the proximal end of the balloon.

Next, heat is applied to a localized area of the first tube 20. Heating may be accomplished by any method currently known in the art, including but not limited to direct current (DC), radiofrequency (RF), inductance and infrared radiation (IR). For example, the first tube could be placed in a die. The die may be made of any material that will not be affected by the heat applied to the working piece. After the first tube has been heated to its softening point, it is compressed to form a region of reduced internal diameter 24. Compression by any method known in the art is suitable. For example, longitudinal compression may be supplied manually or by a clamp. If manual longitudinal compression is the method of choice, predetermined regions of the first tube 20 are manually pressed towards each other. This pressure causes the softened wall of the first tube 10 to form a region of decreased internal diameter 24. Longitudinal compression is commonly employed when a sleeve has been used so that the outer diameter of the first tube remains constant or decreases. The tube 20 may also be compressed radially. If radial compression is employed, the outer diameter of the shaft may decrease as the region of decreased inner diameter is being formed. In either event, a seal is formed between the region of reduced internal diameter 24 of the first tube 20 and the outer diameter of the second tube 30. After the heating and compressing steps, the valve assembly is allowed to air cool, or alternately, may be cooled using forced fluid flow.

Regardless of the technique used, the amount of heat applied and the duration of heating depend upon the composition of the first tube 20. The heat applied must be sufficient to soften the wall of the first tube 20 without affecting the second tube 30. For example, if the first tube 20 is made of Pebax (Polyether block amide), heating should occur at approximately 335–370° F. for about 10–15 seconds.

There are many possible variations of the apparatus and method of the present invention. One variation alleviates the need for the separate element acting as a stop 40 on the second tube 30. In this embodiment, the second tube 30 is a hypotube that is flared at its distal end, the flared portion comprising the stop 40.

Another variation of the preferred embodiment includes the use of a wire. A wire may be used in conjunction with the above described two-tube embodiment. For example, a stiffening wire could be attached to the distal end of the second or inner tube 30. In this instance, the wire adds stiffness to the device but is not necessary for proper orientation of the valve.

Figure 5:
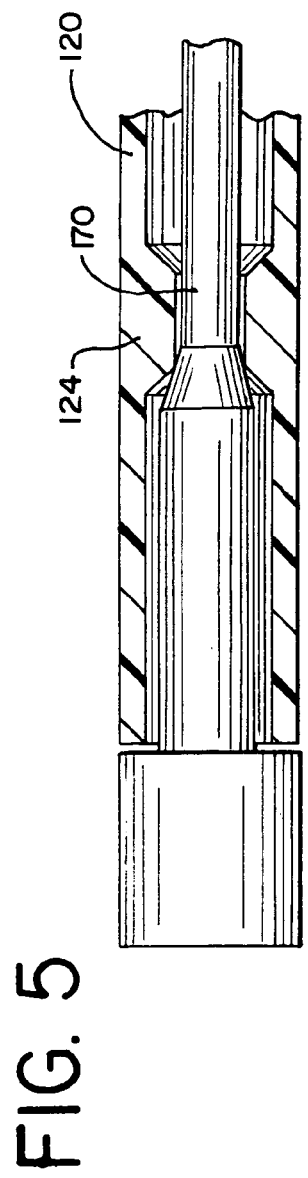
FIG. 5 is a cross-sectional side view of a second preferred embodiment of the low profile inflation valve of the present invention in the closed position.

In another preferred embodiment a wire 170 is used instead of a second or inner tube. Preferably, the wire is tapered at one end. FIG. 5 shows a push/pull design. This design also has a tapered wire 170 that fits within a tube lumen. The outer tube 120 has a region of decreased inner diameter 124. This valve is open when the insert is pulled back to leave space between the wire taper and the region of decreased inner diameter 124. The valve is then closed by moving the wire 170 forward until the taper fits tightly into the region of decreased inner diameter 124. The interference fit between the wire and the region of decreased inner diameter 124 prevents the wire 170 from being pulled out of the first tube 120. In the push/pull design, a stop (not shown) may also be used to prevent the wire 170 from being pulled out of the outer tube 120.

Figure 6:
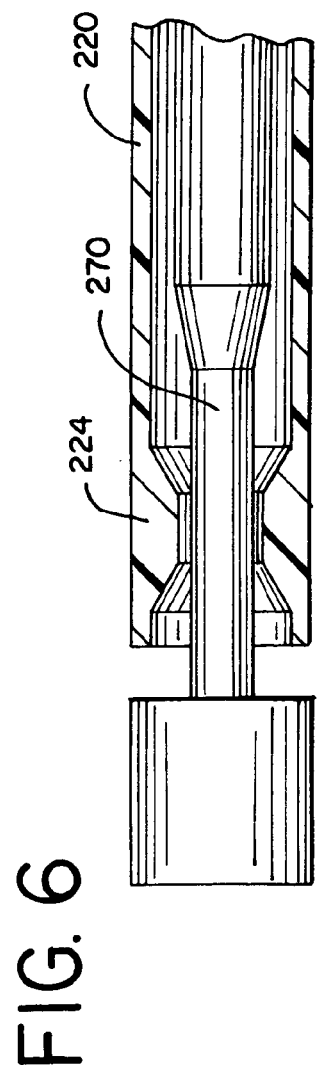
FIG. 6 is a cross-sectional side view of a third preferred embodiment of the low profile inflation valve of the present invention in the inflation position.

FIG. 6 shows another embodiment of the pull/push wire design. In this design, the taper on the wire 270 is distal to the region of reduced inner diameter 224. When the wire 270 is pushed forward there is room between the wire 270 and the outer tube 220 to allow fluid flow. The valve is then closed when the wire 270 is moved back so that the wire taper fits tightly into the region of decreased inner diameter 224 on the outer tube 220. At this point, the interference fit between the wire and the outer tube will vent fluid flow between the two sides of the valve.

Figure 7:
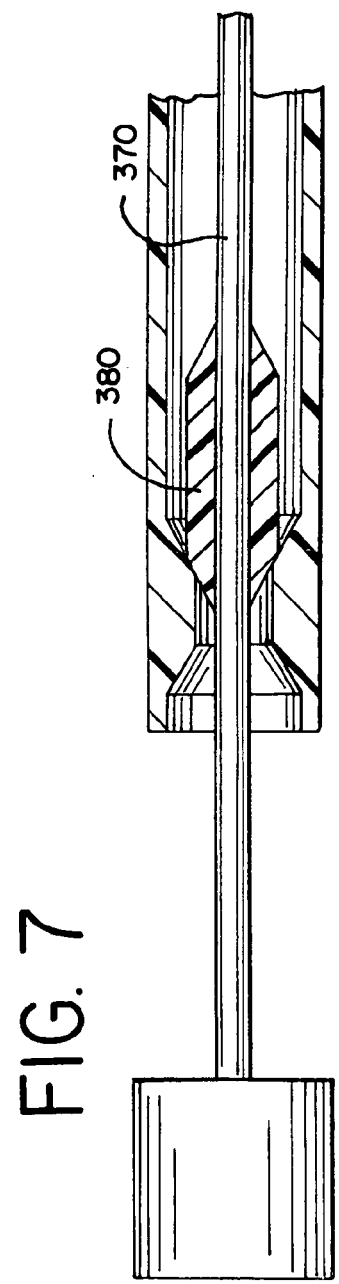
FIG. 7 is a cross-sectional side view of a fourth preferred embodiment of the low profile inflation valve of the present invention in the closed position.

It may not be desirable in some applications to taper the wire insert. In these circumstances, as depicted in FIG. 7, an additional tube or tapered tube 380 can be placed on the wire 370 to perform the same functions as the wire taper.

Figure 8:
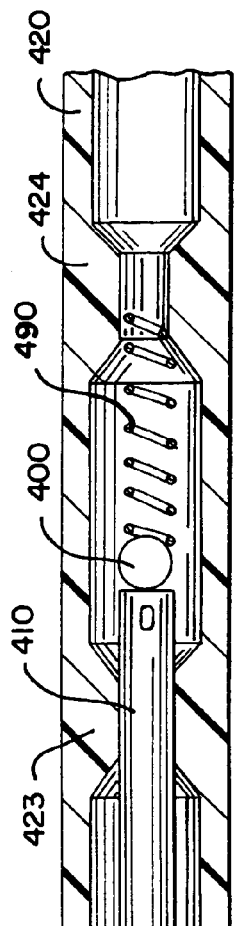
FIG. 8 is a cross-sectional side view of a fifth preferred embodiment of the low profile inflation valve of the present invention in an open position.

Another series of low profile valve designs, illustrated in FIGS. 8–11, use a spring and ball assembly. FIG. 8 shows a ball valve that uses a pin 410 to pressurize and depressurize the system. There are two regions 423 and 424 in which the inner diameter of the first tube 420 is decreased. In this embodiment, the spring 490 is attached to the distal region of reduced inner diameter 424. A ball 400 is attached to the opposite end of the spring 490. The spring's compressive forces force the ball 400 towards the proximal region of decreased inner diameter 423. This is the position that the ball 400 and spring 490 exhibit under normal conditions.

During pressurization of the system, the pin 410 is inserted into the end of the device and pushes the ball 400 forward to the position shown in FIG. 8 to allow fluid to flow around the ball 400 and into the distal region. When the distal region has reached the proper pressure, the pin 410 is removed from the device. The compressive forces in the spring 490 as well as the pressure in the system force the ball 400 against the proximal region of decreased inner diameter 423. At this point, the system is supporting a pressure difference between the two sides of the valve. Depressurization of the system is accomplished by reinserting the pin 410 and pushing the ball 400 forward until fluid can escape out of the system.

The pressurization/depressurization pin 410 can be made in different ways. The pin 410 can be made as a solid wire that is smaller than the proximal region of decreased inner diameter. The fluid enters the system between the pin 410 and the inner diameter of the proximal region of decreased inner diameter. Another option is to use a hypotube with at least one hole towards its distal end. The outer diameter of the hypotube should fit tightly into the region of decreased inner diameter. This pin would be inserted until the distal hole is beyond the region of decreased inner diameter. Fluid then would exit through this inflation hole around the displaced ball and into the system to be pressurized.

Figure 9:
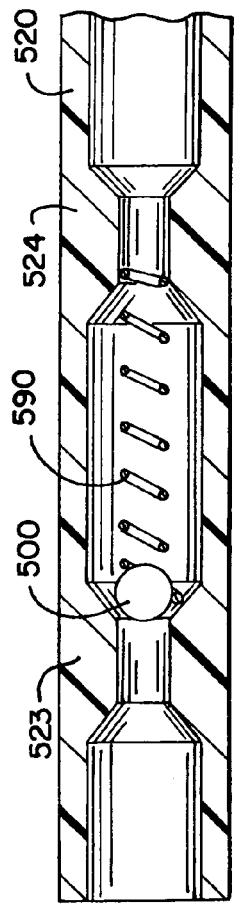
FIG. 9 is a cross-sectional side view of a sixth preferred embodiment of the low profile inflation valve of the present invention in the closed position.

FIG. 9 depicts a ball-spring valve that does not use a pin to pressurize the system. Fluid is injected into the proximal end of the device to pressurize the system. The force of the fluid then forces the ball 500 forward and allows the fluid to enter the distal side of the system. Once the force of inflation halts, the pressure in the system and the force in the spring 590 force the ball 500 against the proximal region of decreased inner diameter 523. Depressurization of the system is accomplished by using a pin 510.

Figure 10:
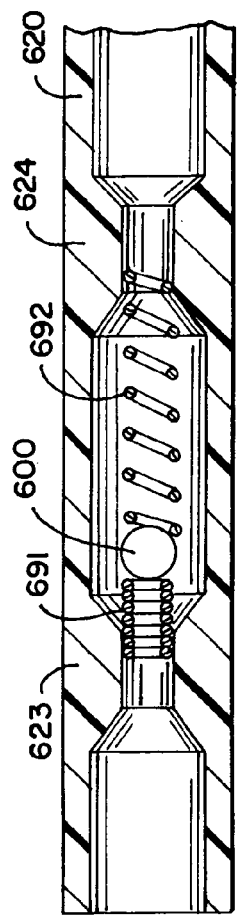
FIG. 10 is a cross-sectional side view of a seventh preferred embodiment of the low profile inflation valve of the present invention in a closed position.
Figure 11:
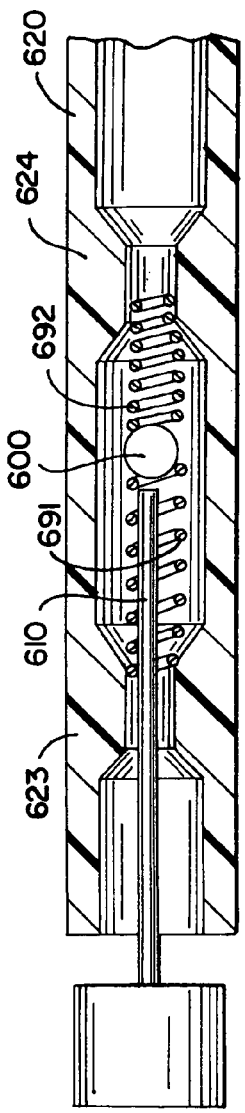
FIG. 11 is a cross-sectional side view of the valve of FIG. 10 in an open position.

FIGS. 10 and 11 show yet another option for a ball-spring valve design. In this embodiment, two springs 691 and 692 are used to support the ball 600. Pressurization is accomplished by either method described above. While holding pressure, the ball 600 is forced toward the proximal spring 691. There must be enough force on the ball 600 to close the loops of the proximal spring 691 and prevent fluid flow between the opposite sides of the device. As shown in FIG. 11, depressurization of the system is then accomplished using a depressurization pin 610.

The ball and springs of FIGS. 8–11 can be made of any suitable material including, but not limited to, stainless steel, nitinol and polymers. The ball does not necessarily have to be spherical. It can be made in any shape that allows it to sit tightly and block the flow of fluid between the two sides of the system.

Other variations involve the method of creating a reduced region of inner diameter. These variations may be beneficial when the valve will be used in conjunction with a catheter body that is not suitable valve material. For example, an additional tube may be inserted into the proximal end of the catheter body. The additional tube can then be used to form the region of decreased inner diameter. In this application, the inserted tube and the catheter body must have similar melting points.

Alternately, the valve material can be bonded or welded to the optimum material. After this is done, the region of reduced inner diameter can be formed by any of the methods disclosed. The outer tube could also be made using intermittent extrusion. This is a continuous extrusion process that can alter the durometer of tubing so that a heat weld would not be necessary. With these methods (heat weld, adhesive bond, or intermittent extrusion), the material used for the valve can be placed anywhere along the shaft of the device.

Another option is to insert a tube into another tube without any further processing. The inner tube would form the region of decreased inner diameter. Another option is to inject a material into the inner diameter of the first tube. Once the material is injected into the inner diameter it cures and secures itself to the inside of the outer tube.

Another possibility is to start with a relatively thick tube. To create a region of reduced inner diameter, a portion of the middle of the tube would be left in its original state while both ends of the tube are drawn out.

Additional options include using different tubes connected in series. A tube made of the valve material may be incorporated that has a smaller inner diameter than the rest of the tubing. The various pieces of tubing can be bonded together using any means commonly used in the industry including, but not limited to, heat bonding and adhesive bonding.

Additional ways of creating a region of decreased inner diameter may encompass necking the first tube. Necking may be accomplished using any method commonly known in the industry. The neck can be formed anywhere on the shaft. What distinguishes the neck from most of the other designs disclosed is that the outer diameter of the tube is decreased during the necking process just as it is during radial compression. An alternate option is to force the material into a hot die so that is closes down the inner diameter of the tubing. This design can only be used if the valve portion is on the end of the shaft. A further option for forming a reduced inner diameter is to place a heat shrinkable material (i.e. Teflon, polyester, etc.) onto the outer diameter of a tube and selectively heat the heat shrinkable material and the corresponding portion of the tube. Preferably, the shrink tube is heated by infrared radiation. The heat shrinkable material will condense, thereby forming a region of decreased inner diameter.

Each of the embodiments of FIGS. 1–11 can be made to have a maximum outer profile of about 0.3 cm. Valves of such small outer profile are unique. They make it possible to use the valve in intravascular medical devices. In addition, they provide a simple, effective means for regulating the pressure in or maintaining a pressure difference between different elements in a medical system. When these valves are incorporated into a balloon catheter, they enable a user to maintain the balloon in an inflated state and exchange other medical apparatus over the catheter.

There are many advantages to the preferred embodiment of the low profile inflation valve of the present invention. Firstly, the new valve has a low profile and therefore enables exchange of various intravascular apparatus over the valve. When the valve is incorporated into a balloon catheter, the valve permits exchange of other devices over an inflated balloon. Secondly, as clearly illustrated in FIG. 3, the seal formed between the region of deceased inner diameter of the first tube and the outer diameter of the second tube effectively controls the pressure inside of a balloon because the inflation fluid is prevented from exiting the catheter lumen through the aperture in the second tube. Thirdly, the valve is easy to use and may be operated by one person like a onehanded stopcock. In addition, the valve can be made to leak above certain pressures and therefore becomes pressure limiting. For example, if the balloon is over inflated, the valve will allow fluid to leak until the balloon pressure is in an acceptable range.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A balloon catheter including a low profile inflation valve comprising:
    a longitudinally extending, non-branching shaft including a proximal end and a distal end with an inflatable balloon adjacent the distal end and an internal surface defining an inflation lumen therein, the lumen being in fluid communication with the balloon such that fluid entering the lumen inflates the balloon; and
    a push/pull wire having a distal portion disposed within a proximal portion of the lumen of the non-branching shaft wherein the push/pull wire is reversibly slidable between an open position which allows fluid from outside of the catheter to flow into the lumen to inflate the balloon and a closed position which blocks fluid from flowing from the balloon, wherein an operator controls the position of the push/pull wire within the lumen between the open and closed position, the push/pull wire being sized such that the operator may maintain the balloon in an inflated state and exchange other medical apparatus over the balloon catheter.

2. The balloon catheter of claim 1, wherein the push/pull wire is moved proximally relative to the longitudinally extending, non-branching shaft to the open position.

3. The balloon catheter of claim 1, wherein the push/pull wire is moved distally relative to the longitudinally extending, non-branching shaft to the closed position.

4. The balloon catheter of claim 1, wherein the push/pull wire is moved distally relative to the longitudinally extending, non-branching shaft to the open position.

5. The balloon catheter of claim 1, wherein the push/pull wire is moved proximally relative to the longitudinally extending, non-branching shaft to the closed position.

6. The balloon catheter of claim 1, wherein the push/pull wire includes a proximal portion of larger outside diameter than a distal portion such that the larger diameter portion limits distal movement of the push/pull wire.

7. The balloon catheter of claim 1, wherein the maximum outside diameter of the push/pull wire over its length is less than or equal to the outside diameter of the longitudinally extending, non-branching shaft.

8. The balloon catheter of claim 1 wherein the inflation lumen has a sealed distal end.

9. A balloon catheter comprising:
    a longitudinally extending, non-branching shaft including a proximal end and a distal end with an inflatable balloon adjacent the distal end and an internal surface defining an inflation lumen therein, the lumen being in fluid communication with the balloon such that fluid entering the lumen inflates the balloon; and
    a valve assembly formed by cooperation between the internal surface of the inflation lumen and a push/pull wire having a distal portion disposed within a proximal portion of the lumen of the non-branching shaft wherein the push/pull wire is reversibly slidable between an open position which allows fluid from outside of the catheter to flow into the lumen to inflate the balloon and a closed position which blocks fluid from flowing from the balloon, wherein an operator controls the position of the push/pull wire within the lumen between the open and closed position, the push/pull wire being sized such that the operator may maintain the balloon in an inflated state and exchange other medical apparatus over the balloon catheter.

10. The balloon catheter of claim 9, wherein the push/pull wire is moved proximally relative to the longitudinally extending, non-branching shaft to the open position.

11. The balloon catheter of claim 9, wherein the push/pull wire is moved distally relative to the longitudinally extending, non-branching shaft to the closed position.

12. The balloon catheter of claim 9, wherein the push/pull wire is moved distally relative to the longitudinally extending, non-branching shaft to the open position.

13. The balloon catheter of claim 9, wherein the push/pull wire is moved proximally relative to the longitudinally extending, non-branching shaft to the closed position.

14. The balloon catheter of claim 9, wherein the push/pull wire includes a proximal portion of larger outside diameter than a distal portion such that the larger diameter portion limits distal movement of the push/pull wire.

15. The balloon catheter of claim 9, wherein the maximum outside diameter of the push/pull wire over its length is less than or equal to the outside diameter of the longitudinally extending, non-branching shaft.

16. The balloon catheter of claim 9 wherein the inflation lumen has a sealed distal end.

17. A balloon catheter including a low profile inflation valve comprising:
    an elongate shaft including a proximal end and a distal end with an inflatable balloon adjacent the distal end and an internal surface defining an inflation lumen therein, the lumen being in fluid communication with the balloon; and
    an elongate member having a distal portion disposed within the elongate shaft and a proximal portion accessible from outside the elongate shaft, the elongate member being longitudinally moveable within the elongate shaft in response to pushing and/or pulling forces applied to the proximal portion; wherein:
    when the elongate member is in a first longitudinal position with respect to the elongate shaft, fluid is prevented from passing through the inflation lumen; and
    when the elongate member is in a second longitudinal position with respect to the elongate shaft, fluid is allowed to pass through the inflation lumen.

* * * * *

UNITED STATES PATENT AND TRADEMARK OFFICE
CERTIFICATE OF CORRECTION

PATENT NO. : 6,926,729 B1  
DATED : August 9, 2005  
INVENTOR(S) : Jonathan C. Sell et al.

It is certified that error appears in the above-identified patent and that said Letters Patent is hereby corrected as shown below:

Column 1,
Line 17, after "multitude" and before "medical", insert -- of --.

Column 6,
Line 51, delete "vent" and insert therefor -- prevent --.

Signed and Sealed this

Eleventh Day of October, 2005

JON W. DUDAS
*Director of the United States Patent and Trademark Office*